United States Patent
Hefner et al.

(10) Patent No.: US 8,643,389 B2
(45) Date of Patent: Feb. 4, 2014

(54) CORROSION SENSOR AND METHOD FOR MANUFACTURING A CORROSION SENSOR

(75) Inventors: Rebecca Evelyn Hefner, Simpsonville, SC (US); Paul Stephen DiMascio, Greer, SC (US)

(73) Assignee: General Electric Company, Schenectady, NY (US)

( * ) Notice: Subject to any disclaimer, the term of this patent is extended or adjusted under 35 U.S.C. 154(b) by 351 days.

(21) Appl. No.: 12/985,541

(22) Filed: Jan. 6, 2011

(65) Prior Publication Data

US 2012/0176147 A1   Jul. 12, 2012

(51) Int. Cl.
| | |
|---|---|
| G01R 1/067 | (2006.01) |
| C23C 14/54 | (2006.01) |
| G01F 1/64 | (2006.01) |
| G01N 17/02 | (2006.01) |
| G01N 17/04 | (2006.01) |
| C25D 17/00 | (2006.01) |
| C25D 21/12 | (2006.01) |

(52) U.S. Cl.
USPC ........ 324/700; 324/755.01; 427/9; 205/775.5

(58) Field of Classification Search
CPC ....... G01N 17/02; G01N 17/04; C25D 17/00; C25D 21/12
USPC .......... 324/700, 755.01; 205/775.5; 427/9–58
See application file for complete search history.

(56) References Cited

U.S. PATENT DOCUMENTS

| | | | |
|---|---|---|---|
| 4,818,725 A | 4/1989 | Lichtel et al. | |
| 5,100,501 A | 3/1992 | Blumenthal et al. | |
| 5,132,248 A | 7/1992 | Drummond et al. | |
| 5,244,538 A * | 9/1993 | Kumar | 216/18 |
| 5,306,414 A | 4/1994 | Glass et al. | |
| 6,132,593 A | 10/2000 | Tan | |
| 6,830,778 B1 | 12/2004 | Schulz et al. | |
| 2002/0012743 A1 | 1/2002 | Sampath et al. | |
| 2003/0087040 A1 | 5/2003 | Ladentin | |
| 2004/0114666 A1 | 6/2004 | Hardwicke et al. | |
| 2004/0121182 A1 | 6/2004 | Hardwicke et al. | |
| 2007/0193887 A1 * | 8/2007 | Tormoen et al. | 205/775.5 |
| 2008/0003353 A1 | 1/2008 | Hardwicke et al. | |
| 2008/0169205 A1 * | 7/2008 | Kim | 205/775.5 |
| 2008/0217172 A1 | 9/2008 | Chiang et al. | |
| 2009/0015271 A1 * | 1/2009 | Elliott | 324/690 |
| 2009/0061169 A1 * | 3/2009 | Khaselev et al. | 428/195.1 |
| 2010/0253375 A1 * | 10/2010 | Fang et al. | 324/754 |
| 2010/0288543 A1 | 11/2010 | Hung et al. | |
| 2011/0118655 A1 * | 5/2011 | Fassih et al. | 604/20 |

OTHER PUBLICATIONS

Search Report and Written Opinion from corresponding EP Application No. 11195288.3-2204 dated Apr. 11, 2012.
Hon, K. K. B. et al., "Direct writing technology—Advances and developments", CIRP Annals, vol. 57, No. 2, pp. 601-620, Jan. 1, 2008.

* cited by examiner

*Primary Examiner* — Melissa Koval
*Assistant Examiner* — Farhana Hoque
(74) *Attorney, Agent, or Firm* — Dority & Manning, PA (57) ABSTRACT

A corrosion sensor includes a plurality of conductive portions and at least one non-conductive portion between adjacent conductive portions, wherein the at least one non-conductive portion has a dimension less than approximately 500 microns. A method for manufacturing a corrosion sensor includes applying a non-conductive material to a substrate and applying a conductive material to discrete locations on the non-conductive material. The method further includes applying a brazing material around each discrete location of the conductive material.

19 Claims, 6 Drawing Sheets

CORROSION SENSOR AND METHOD FOR MANUFACTURING A CORROSION SENSOR

FIELD OF THE INVENTION

The present invention generally involves a corrosion sensor and methods for manufacturing the corrosion sensor.

BACKGROUND OF THE INVENTION

Machinery and equipment operated in harsh environments are often subject to accelerated corrosion rates which, if not monitored or controlled, can result in premature aging and eventually failure of the machinery and equipment. For example, in a gas turbine, high temperature combustion gases flow along a hot gas path through a turbine to produce work. The combustion gases may include sufficient quantities of oxygen to produce general corrosion on the metal surfaces along the hot gas path. The general corrosion is characterized by an oxidation-reduction reaction in which the metal surfaces are oxidized, producing an anode at the oxidation site and a cathode at the reduction site.

Figure 1:
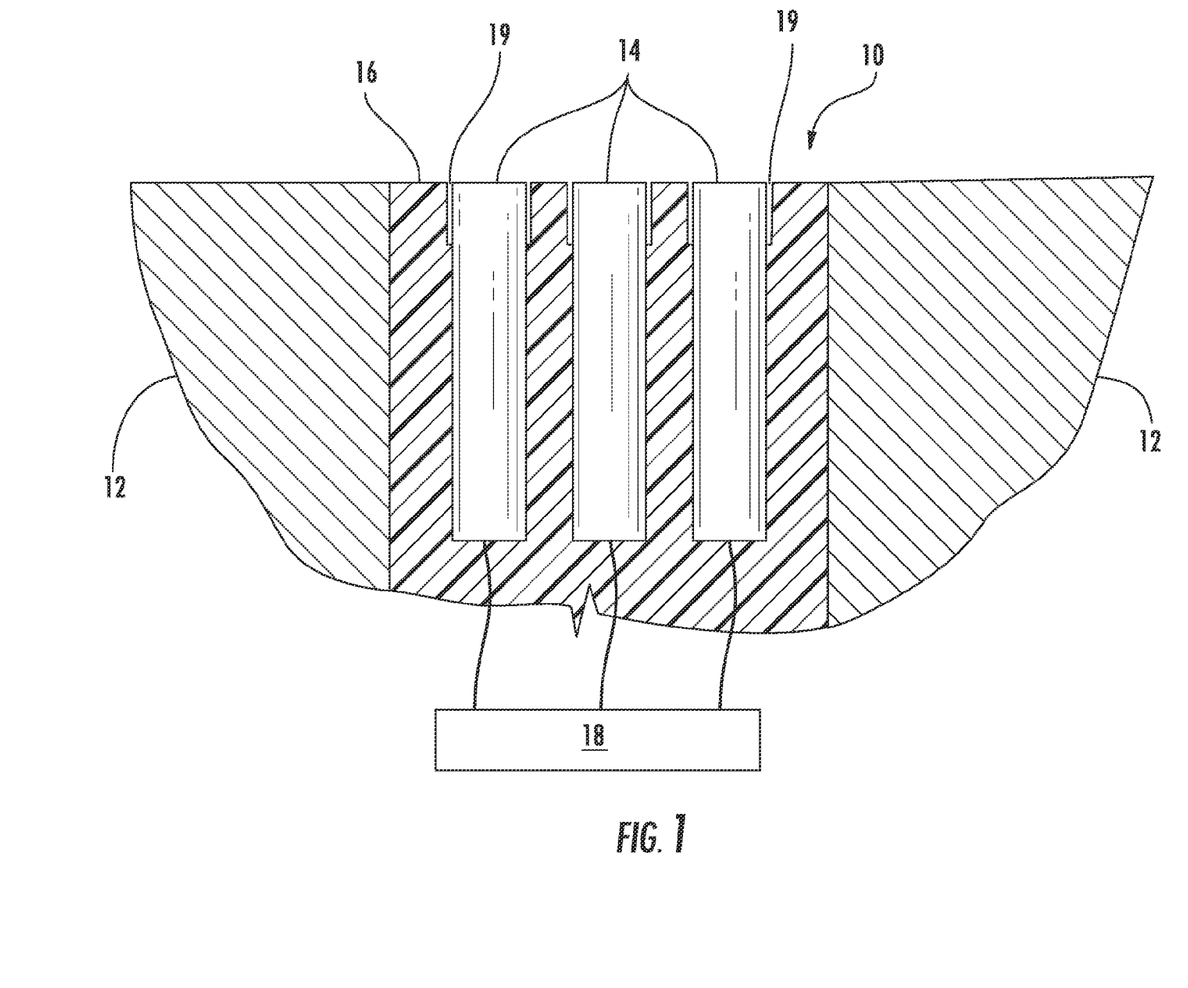
FIG. 1 is a simplified side cross-section view of a conventional corrosion sensor.

Sensors may be installed on the metal surfaces to monitor the presence and/or rate of any general corrosion. For example, as shown in FIG. 1, a conventional corrosion sensor 10 installed on a metal surface 12 may comprise alternating layers of electrodes 14 separated by dielectric material 16. The electrodes 14 may have an oxidation potential comparable to that of the metal surfaces 12 so that the general corrosion rate on the metal surfaces 12 may be approximated by the general corrosion rate on the electrodes 14. The general corrosion rate occurring on the metal surfaces 12 may thus be determined using a sensor 18 to measure the electrical potential or current flow across the electrodes 14.

The bond or interface between the electrodes 14 and the dielectric material 16 in the conventional corrosion sensor 10 may degrade over time, creating small gaps 19 or other low flow regions between the electrodes 14 and dielectric material 16, as shown in FIG. 1. These gaps 19 or low flow regions result in a local area conducive to crevice corrosion. Crevice corrosion between the electrodes 14 and dielectric material 16 exposes a larger surface area of the electrodes 14 to the hot gas path, increasing the electrical potential or current flow across the electrodes 14 for the same general corrosion rate. As a result, crevice corrosion changes the calibration and/or accuracy of the conventional corrosion sensors 10 over time. Therefore, a corrosion sensor and method for manufacturing a corrosion sensor resistive to crevice corrosion would be useful.

BRIEF DESCRIPTION OF THE INVENTION

Aspects and advantages of the invention are set forth below in the following description, or may be obvious from the description, or may be learned through practice of the invention.

One embodiment of the present invention is a corrosion sensor that includes a plurality of conductive portions and at least one non-conductive portion between adjacent conductive portions. The at least one non-conductive portion between adjacent conductive portions has a dimension less than approximately 500 microns.

Another embodiment of the present invention is a method for manufacturing a corrosion sensor that includes applying a non-conductive material on a substrate and applying a conductive material at discrete locations on the non-conductive material. The method further includes applying a brazing material around each discrete location of the conductive material.

A still further embodiment of the present invention is a method for manufacturing a corrosion sensor that includes applying a filler material to a substrate and applying a binder material to discrete locations on the substrate to form conductive portions at the discrete locations on the substrate. The method further includes applying a brazing material around each discrete location of the conductive material.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Embodiments of the present invention provide a corrosion sensor and methods for manufacturing the corrosion sensor that is believed to be more sensitive to detecting and measuring general corrosion and/or more resistant to crevice corrosion known to degrade the sensitivity and accuracy of conventional corrosion sensors. The various embodiments generally benefit from direct write deposition techniques that allow for the repeatable and reliable production of smaller electrodes that are spaced closer together. In addition, the direct write deposition techniques employed by embodiments of the present invention produce a generally seamless interface or joint between the conducting portions and non-conducting portions of the corrosion sensor to reduce and/or prevent crevice corrosion from degrading the corrosion sensor over time.

Figure 2:
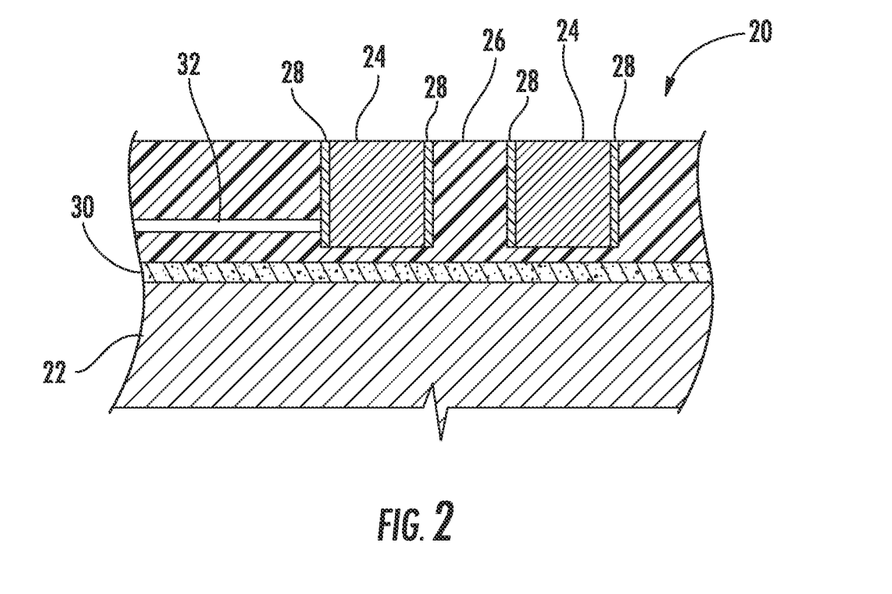
FIG. 2 is a simplified side cross-section view of a corrosion sensor according to one embodiment of the present invention.
Figure 3:
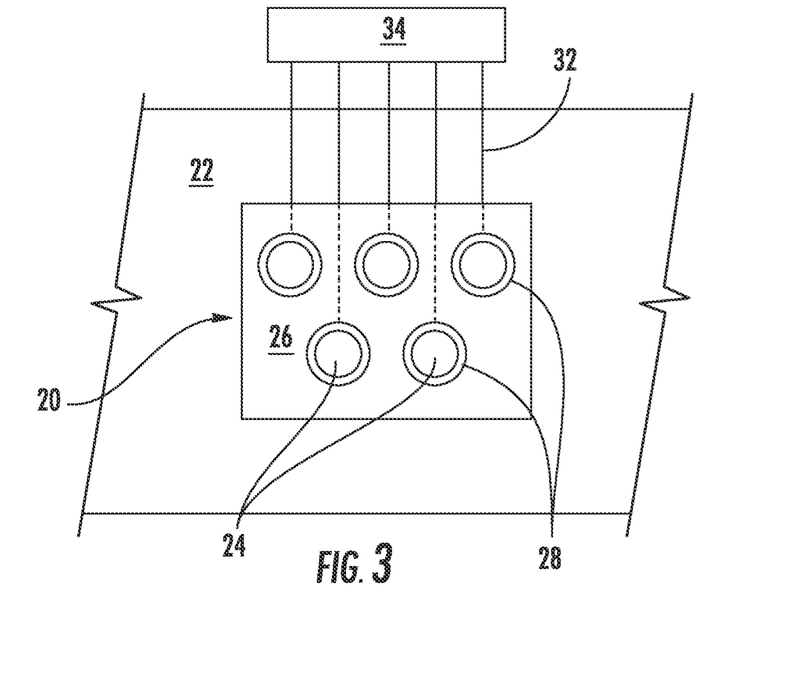
FIG. 3 is a top plan view of the corrosion sensor shown in FIG. 2.

FIG. 2 provides a simplified side cross-section view of a corrosion sensor 20 according to one embodiment of the present invention, and FIG. 3 provides a simplified top plan view of the corrosion sensor 20 shown in FIG. 2. The corrosion sensor 20 is designed to be installed in or on a metallic substrate 22 to monitor and/or measure the presence or rate of general corrosion occurring on the metallic substrate 22. During operations, the corrosion sensor 20 experiences general corrosion at approximately the same rate as the metallic substrate 22, and the current flow and/or electrical potential produced by the corrosion sensor 20 may be measured to determine the general corrosion rate of the metallic substrate 22.

As shown, a particular embodiment of the corrosion sensor 20 may include a plurality of conductive portions 24, at least one non-conductive portion 26, and a seamless joint 28 between the conductive and non-conductive portions 24, 26. The conductive portions 24 may comprise platinum, palladium, gold, silver, copper, combinations or blends thereof, or other highly conductive materials known in the art. In addition, the conductive portions 24 may be doped with additional materials so that the conductive portions 24 have an oxidation potential comparable to the metallic substrate 22. Although depicted as cylindrical in shape, the conductive portions 24 may take any geometric shape. The at least one non-conductive portion 26 may surround and electrically insulate the conductive portions 24 and may comprise any non-conductive material suitable for the temperatures and pressures anticipated for the metallic substrate 22. For example, the non-conductive portion(s) 26 may comprise dielectric material, ceramics, or other suitable non-conductive materials known in the art. The manufacturing methods disclosed herein generally allow fabrication of smaller and more closely spaced conductive portions 24 than in conventional corrosion sensors. For example, the conductive portions 24 manufactured according to various embodiments of the present invention may have a dimension exposed to general corrosion of less than approximately 500 microns, and in some embodiments as small as approximately 5 microns. Alternately, or in addition, the spacing between adjacent conductive portions 24 may result in the non-conductive portion 26 between adjacent conductive portions 24 having a dimension less than approximately 500 microns, and in some embodiments as small as approximately 5 microns.

The seamless joint 28 or connection between the conductive and non-conductive portions 24, 26 reduces and/or prevents crevice corrosion from occurring between the conductive and non-conductive portions 24, 26. The seamless joint 28 may comprise, for example, a metallurgical bond such as a brazed joint between the conductive and non-conductive portions 24, 26.

The corrosion sensor 20 may be attached directly to the metallic substrate 22, for example, by an adhesive material. Alternatively, as shown in FIG. 2, an optional bond coat layer 30 may be included between the corrosion sensor 20 and the metallic substrate 22 to minimize any chemical or electrical interaction between the corrosion sensor 20 and the metallic substrate 22 and/or to provide improved adhesion between the corrosion sensor 20 and the metallic substrate 22. The optional bond coat layer 30 may comprise, for example, alumina, a thermal barrier coating, or another layer to enhance the adherence between the corrosion sensor 20 and the metallic substrate 22. As shown in FIGS. 2 and 3, electrodes 32 may connect each conductive portion 24 to an electrical sensor 34. The electrodes 32 may comprise a conductive wire, perhaps formed from the same conductive material and in the same manner as the conductive portions 24, and may be embedded in the corrosion sensor 20 for conducting current flow between the conductive portions 24 and the electrical sensor 34. The electrical sensor 34 may comprise a voltmeter, an ammeter, or another suitable sensor for measuring the electrical potential and/or current flow between the conductive portions 24. In this manner, the voltage or current flow between the conductive portions 24 may be used to determine the general corrosion rate of the substrate material 22.

Figure 4:
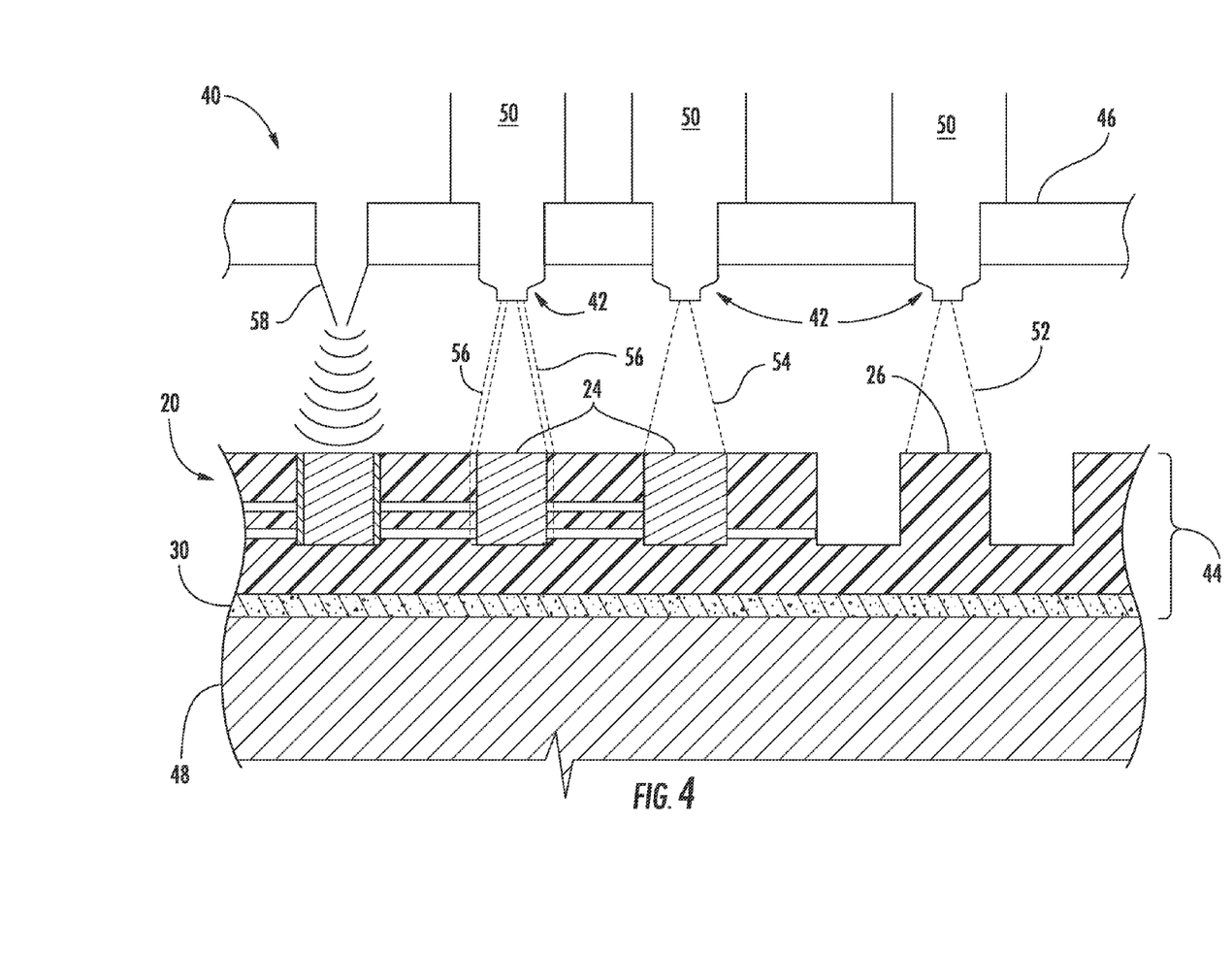
FIG. 4 is a simplified side cross-section view of a direct write deposition system for manufacturing a corrosion sensor according to one embodiment of the present invention.

The corrosion sensor 20 described and illustrated in FIGS. 2 and 3 may be manufactured using one of several direct write deposition techniques. As used herein, "direct write deposition techniques" include dip pen nanolithography, micropen writing, laser particle guidance or laser jet printing, plasma spraying, laser assisted chemical vapor deposition, ink jet printing, and transfer printing, any of which may be adapted to manufacture corrosion sensors 20 within the scope of the present invention. For example, FIG. 4 shows a direct write deposition system 40 for manufacturing corrosion sensors 20 according to various embodiments of the present invention. As shown, the system 40 may include a plurality of nozzles 42 directed at a work piece 44, with relative motion between the nozzles 42 and the work piece 44. For example, the nozzles 42 may be attached to one or more arms 46 or assemblies configured to move each nozzle 42 with respect to the stationary work piece 44. Alternatively, or in addition, the work piece 44 may be located on a conveyor 48 or other surface configured to move the work piece 44 with respect to the nozzles 42.

Each nozzle 42 may be connected to a separate supply of material dedicated to that particular nozzle 42. Alternately, multiple supplies of materials may be multiplexed through a single nozzle 42. Each supply of material may include a pump, a container 50, a mixer, and other associated equipment for supplying the material to be deposited onto the work piece 44. The material to be deposited may comprise fine powders ranging in size on the order of 10 nanometers to several hundred microns. The fine powders may be suspended in a solvent, such as alcohol or water, that may further include fillers or binders such as starch, cellulose, surfactants, and other additives to adjust the rheological properties of the material. The nozzle diameter and rheology of the supplied material generally determine the minimum and maximum dimensions of the deposited material. For example, nozzles 42 having a diameter of 25-600 microns may readily produce deposits in dimensions ranging from approximately 1-600 microns in width and 1-10 microns in thickness per pass, with the number of passes dependent on the desired thickness of the deposited material.

As shown in FIG. 4, for example, the system 40 may include separate nozzles 42 dedicated for depositing non-conductive material 52, conductive material 54, and brazing material 56 onto the work piece 44. As the nozzles 42 move with respect to the work piece 44, a controller (not shown) may execute a CAD/CAM or similar program to actuate each nozzle 42 as desired to deposit the specific material onto discrete locations on the work piece 44. For example, the controller may actuate the nozzles 42 to sequentially deposit the non-conductive material 52, conductive material 54, and brazing material 56 onto the bond coat 30 during multiple passes to form the corrosion sensor 20 as shown in FIG. 4. The resulting deposition layers may be cured between successive passes of the nozzles 42 or when the desired thicknesses are achieved using conventional curing devices, such as, for example, ovens, lamps, and other heat sources. Alternately, as shown in FIG. 4, a source 58 may be integrated with the system 40 to cure the resulting deposition layer and/or braze the conductive and non-conductive portions 24, 26 using, for example, ultraviolet, ultrasonic, thermal, or other forms of heat.

Multiple variations of the exemplary direct write system 40 shown in FIG. 4 may be used to manufacture corrosion sensors 20 within the scope of the present invention. For example, the system 40 may include one nozzle supplied with the non-conductive filler material 52 to be infiltrated, a second nozzle supplied with the conductive material 54 or slurry, and a third nozzle supplied with the brazing material 56 or slurry. The first nozzle may thus deposit a uniform base coat of the filler material 52 onto the bond coat 30, if present, or metallic substrate 22 during an initial pass or series of passes. The second nozzle may then deposit the conductive material 54 at discrete locations to mix with the filler material 52 in the base coat, and the third nozzle may deposit the brazing material 56 around each discrete location of the conductive material 54. Sintering or other curing may then be performed to the resulting deposition layers to produce any of the corrosion sensors 20 illustrated in FIGS. 2-4.

Figure 5:
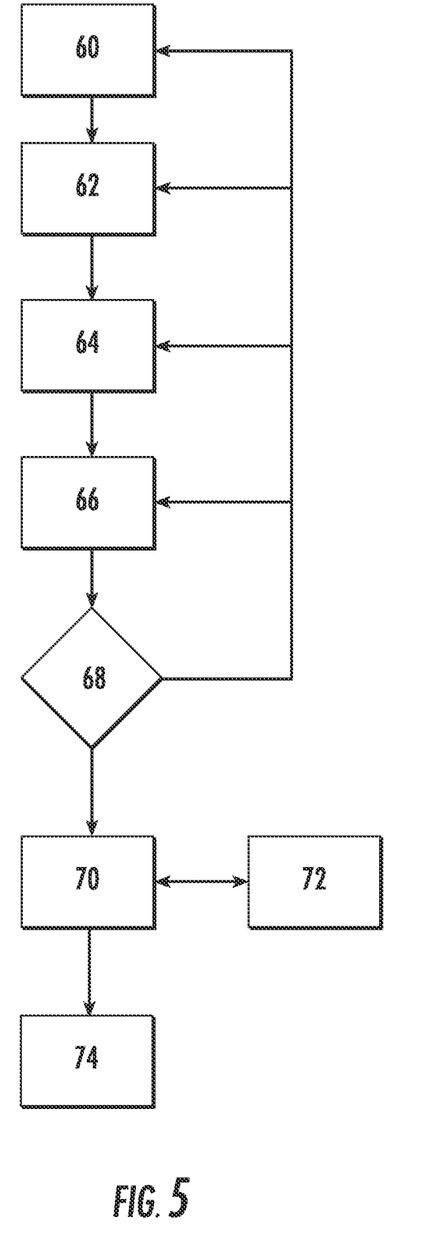
FIG. 5 is a flow diagram of a method for manufacturing corrosion sensors according to one embodiment of the present invention.

Method 1: FIG. 5 provides a flow diagram of a first method for manufacturing corrosion sensors 20, for example using the system 40 described and shown in FIG. 4. At block 60, a thin layer of non-conductive or filler material 52 may be deposited, sprayed, printed, or otherwise applied to the substrate, such as, for example the bond coat 30 or directly to the metallic substrate 22 being monitored for corrosion. At block 62, during the same or subsequent passes, a thin layer of conductive or binder material 54 may similarly be deposited, sprayed, printed, or otherwise applied at specific or discrete locations, and at block 64, a brazing material 56 may be deposited, sprayed, printed, or otherwise applied around each discrete location of the conductive or binder material 54.

One of ordinary skill in the art will readily appreciate that one or more of the filler material 52, binder material 54, and/or brazing material 56 may be applied as a dry nano-powder, a liquid, or a slurry of fine powders suspended in a solvent, such as alcohol or water, that may further include fillers or binders such as starch, cellulose, surfactants, and other additives to adjust the rheological properties of the material. In addition, the non-conductive or filler material 52, the conductive or binder material 54, and/or the brazing material 56 may be selected or doped to have similar melting points to one another. In this manner, the nozzles 42 may deposit, spray, print, or otherwise apply the conductive or binder material 54 to produce conductive portions 24 having a dimension of less than approximately 500 microns, and in some embodiments as small as approximately 5 microns. In addition, the spacing between adjacent conductive portions 24 may result in the non-conductive portion 26 between adjacent conductive portions 24 having a dimension less than approximately 500 microns, and in some embodiments as small as approximately 5 microns.

At block 66, the source 58 may be energized to cure the previously applied filler material 52, binder material 54, and/or brazing material 56, for example such as by using ultraviolet, ultrasonic, thermal, or other forms of heat appropriate for the particular filler, binder, and brazing materials 52, 54, 56 being used. Curing of the non-conductive or filler material 52 produces the non-conductive portions 26. Curing of the conductive or binder material 54 mixed with the filler material 52 produces the conductive portions 24 and/or electrodes 32. Curing of the brazing material 56 around each discrete location of the conductive or binder material 54 produces the seamless joint or metallurgical bond 28 between the conductive and non-conductive portions 24, 26.

At block 68, the thickness of the various layers are checked, and one or more of blocks 60, 62, 64 and/or 66 may be repeated, as desired, to increase the thickness of the conductive portions 24, non-conductive portions 26, and/or seamless joint 28 on the corrosion sensor 20. Once the desired thickness of each layer is achieved, the process continues to block 70 where electrodes 32, if not previously formed in concert with the conductive portions 24, may be connected to each discrete location of the conductive material 24. If desired, the electrodes 32 may be pretreated or conditioned to create an adherent oxide layer resistant to crevice corrosion on the surface of the electrodes, as represented by block 72. The pretreatment or conditioning of the electrodes 32 may take place after each layer is applied to the substrate. Alternately, the pretreatment or conditioning of the electrodes 32 may take place as a final finishing process. At block 74, the electrodes 32 may be connected to the electrical sensor 34 so that the electrical sensor 34 is connected to each discrete location of the conductive material 24.

Figure 6:
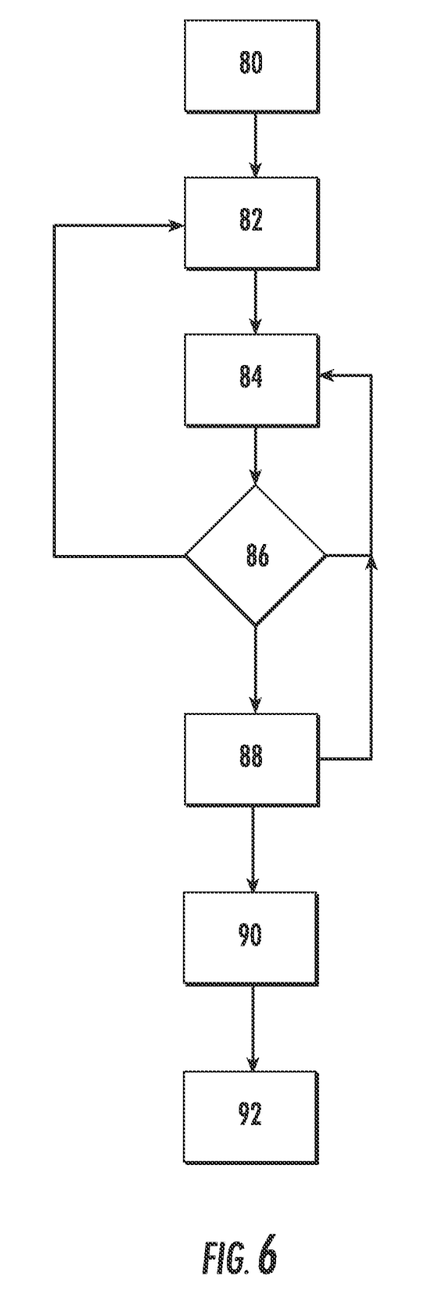
FIG. 6 is a flow diagram of a method for manufacturing a corrosion sensor according to a second embodiment of the present invention.

Method 2: FIG. 6 provides a flow diagram of a method for manufacturing corrosion sensors 20 according to a second embodiment of the present invention. At block 80, a first layer of non-conductive material 26 may be deposited, sprayed, printed, or otherwise applied to the substrate. The substrate may comprise, for example, the bond coat 30 or the metallic substrate 22 being monitored for corrosion and may already include electrodes 32 pre-positioned at desired locations to connect to the subsequently applied conductive portions 24. At block 82, the conductive portions 24 may be written onto the non-conductive material 26 in particular locations in a manner similar to writing with an ink pen. For example, a metal in solution, such as a molten metal or a metal powder in a liquid solution, may be written onto the non-conductive material 26 to form the desired patterns of the conductive portions 24. As previously described, the specific locations of the conductive portions 24 may result in a dimension of less than approximately 500 microns, and in some embodiments as small as approximately 5 microns. In addition, the spacing between adjacent conductive portions 24 may result in the non-conductive portion 26 between adjacent conductive portions 24 having a dimension less than approximately 500 microns, and in some embodiments as small as approximately 5 microns.

At block 84, the resulting conductive and non-conductive portions 24, 26 may be cured, for example using ultraviolet, ultrasonic, thermal, or other forms of heat appropriate for the particular materials being used. At block 86, the thickness of the various layers is checked. If desired, the writing (block 82) and/or curing (block 84) process may be repeated with additional layers of the metal repeatedly written onto the previously cured conductive portions 24 to build up the conductive portions 24 at specific locations to be thicker than the underlying electrodes 32 being used.

When the desired thickness of the conductive portions 24 is achieved, the process continues to block 88 where a second or final layer of the non-conductive material 26 may be applied over the entire surface, covering both the conductive and non-conductive portions 24, 26. A final curing step may be repeated, if desired. At block 90, a portion of the second or final layer of the non-conductive material 26 may be lightly machined to expose the surface of the conductive portions 24 without exposing the underlying electrodes 32. At block 92, the electrical sensor 34 may be connected to each of the conductive portions 24 and/or electrodes 32 to produce the corrosion sensor 20 with the seamless joint 28 between the conductive and non-conductive portions 24, 26.

Figure 7:
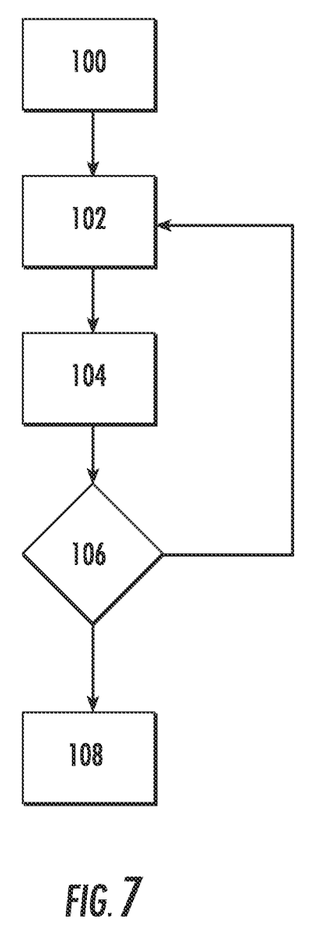
FIG. 7 is a flow diagram of a method for manufacturing a corrosion sensor according to a third embodiment of the present invention.

Method 3: FIG. 7 provides a flow diagram of a method for manufacturing corrosion sensors 20 according to a third embodiment of the present invention. In this particular method, the corrosion sensors 20 may be formed using thermal spray or cold spray techniques, such as, for example, high velocity oxy-fuel, thermal spray, or cold spray techniques. Specifically, at block 100, the non-conductive material 26 may be sprayed onto the substrate using a thermal spray or cold spray technique known in the art. The substrate may again comprise, for example, the bond coat 30 or the metallic substrate 22 being monitored for corrosion and may already include electrodes 32 at desired locations to connect to the subsequently applied conductive portions 24. At block 102, the conductive portions 24 may be sprayed onto the substrate and/or non-conductive material 26 in particular locations to achieve the desired pattern or spacing of conductive and non-conductive portions 24, 26 across the substrate, as previously described with respect to Methods 1 and 2. Specifically, the specific locations of the conductive portions 24 may result in a dimension of less than approximately 500 microns, and in some embodiments as small as approximately 5 microns. In addition, the spacing between adjacent conductive portions 24 may result in the non-conductive portion 26 between adjacent conductive portions 24 having a dimension less than approximately 500 microns, and in some embodiments as small as approximately 5 microns. At block 104, the non-conductive material 26 may be sprayed around the previously applied conductive portions 24 to fill the space between the conductive portions 24 and diffuse with the conductive portions 24 to form the seamless bond 28 between the conductive and non-conductive portions 24, 26.

At block 106, the thickness of the sensor 20, particularly the thickness of the conductive material 24 at discrete locations, is checked. If desired, the process of spraying conductive portions 24 at discrete locations (block 102) and non-conductive portions 26 around the conductive portions 24 (block 104) may be repeated as necessary to achieve a desired thickness of the conductive and non-conductive portions 24, 26. When the desired thickness of the conductive and non-conductive portions 24, 26 is achieved, the process continues to block 108 where the electrical sensor 34 may be connected to each of the conductive portions 24 or electrodes 32 to produce the corrosion sensor 20 with the seamless bond 28 between the conductive and non-conductive portions 24, 26.

It is believed that one or more of the previously described direct write deposition techniques will allow the manufacture of corrosion sensors 20 within the scope of the present invention with one or more benefits over the existing technology. For example, the techniques described herein will allow for the repeatable, cost-effective production of corrosion sensors 20 having smaller conductive portions 24 capable of detecting and/or measuring smaller amounts of aqueous or molten salt corrosion. The smaller sized corrosion sensors 20 will also be suitable for smaller environments that were previously too small to accommodate a corrosion sensor. In addition, the seamless metallurgical joint 28 between the conductive and non-conductive portions 24, 26 reduces the occurrence of crevice corrosion to enhance the accuracy and reliability of the corrosion sensors 20 over time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other and examples are intended to be within the scope of the claims if they include structural elements that do not differ from the literal language of the claims, or if they include equivalent structural elements with insubstantial differences from the literal languages of the claims.

What is claimed is:

1. A corrosion sensor comprising:
   a. a plurality of laser printed conductive portions;
   b. at least one laser printed non-conductive portion between adjacent laser printed conductive portions, wherein the at least one laser printed non-conductive portion between adjacent laser printed conductive portions has a dimension less than approximately 500 microns;
   c. a metallurgical bond between the laser printed conductive portions and the at least one laser printed non-conductive portion between adjacent laser printed conductive portions; and
   d. wherein the laser printed brazing material around each discrete location of the conductive material is cured to form a seamless joint between the laser printed non-conductive material and the laser printed conductive material.

2. The corrosion sensor as in claim 1, wherein the at least one laser printed non-conductive portion between adjacent laser printed conductive portions has a dimension less than approximately 5 microns.

3. The corrosion sensor as in claim 1, wherein each of the plurality of laser printed conductive portions has a dimension less than approximately 500 microns.

4. A method thr manufacturing a corrosion sensor comprising:
   a. printing a non-conductive material to a substrate;
   b. printing a conductive material to discrete locations on the non-conductive material;
   c. printing a brazing material around each discrete location of the conductive material; and
   d. curing the printed brazing material around each discrete location of the conductive material to form a seamless joint between the printed non-conductive material and the printed conductive material.

5. The method as in claim 4, further comprising printing the conductive material so that the discrete locations have a dimension less than approximately 500 microns.

6. The method as in claim 4, further comprising printing the conductive material so that the distance between the discrete locations of conductive material is less than approximately 500 microns.

7. The method as in claim 4, further comprising printing the conductive material so that the distance between the discrete locations of conductive material is less than approximately 5 microns.

8. The method as in claim 4, further comprising curing at least one of the non-conductive material or the conductive material.

9. The method as in claim 4, further comprising brazing the non-conductive material to the conductive material.

10. The method as in claim 4, further comprising connecting an electrode to each discrete location of the conductive material.

11. The method as in claim 10, further comprising forming an oxide layer on the electrodes.

12. The method as in claim 4, further comprising connecting an electrical sensor to each discrete location of the conductive material.

13. A method for manufacturing a corrosion sensor comprising:
   a. printing a filler material to discrete locations of a substrate to form non-conductive portions at the discrete locations of the substrate;
   b. printing a binder material to discrete locations on the substrate to form conductive portions at the discrete locations on the substrate, wherein each of the conductive portions are separated from each of the non-conductive portions by a gap;
   c. printing a brazing material in each gap around each discrete location of the conductive portions; and
   d. curing the printed brazing material to form a seamless metallurgical bond between the non-conductive portions and the conductive portions.

14. The method as in claim 13, further comprising printing the binder material so that the discrete locations have a dimension less than approximately 500 microns.

15. The method as in claim 13, further comprising printing the binder material so that the distance between discrete locations of conductive portions is less than approximately 500 microns.

16. The method as in claim 13, further comprising brazing a non-conductive material to the conductive portions.

17. The method as in claim 13, further comprising connecting an electrode to each discrete location of the conductive portions.

18. The method as in claim 17, further comprising forming an oxide layer on the electrodes.

19. The method as in claim 13, further comprising connecting an electrical sensor to each discrete location of the conductive portions.

* * * * *